(12) United States Patent
Yasukawa

(10) Patent No.: US 10,401,310 B2
(45) Date of Patent: Sep. 3, 2019

(54) X-RAY STRESS ANALYSIS APPARATUS, METHOD, AND PROGRAM

(71) Applicant: Rigaku Corporation, Akishima-shi, Tokyo (JP)

(72) Inventor: Shoichi Yasukawa, Hino (JP)

(73) Assignee: RIGAKU CORPORATION, Tokyo (JP)

( * ) Notice: Subject to any disclaimer, the term of this patent is extended or adjusted under 35 U.S.C. 154(b) by 206 days.

(21) Appl. No.: 15/232,936

(22) Filed: Aug. 10, 2016

(65) Prior Publication Data

US 2017/0082561 A1    Mar. 23, 2017

(30) Foreign Application Priority Data

Sep. 18, 2015    (JP) .................................. 2015-186004

(51) Int. Cl.
*G01N 23/205*    (2018.01)
*G01N 23/207*    (2018.01)

(52) U.S. Cl.
CPC ......... *G01N 23/207* (2013.01); *G01N 23/205* (2013.01); *G01N 2223/607* (2013.01)

(58) Field of Classification Search
CPC .. G01N 23/20; G01N 23/207; G01N 23/2076; G01N 2223/00; G01N 2223/05; G01N 2223/056; G01N 2223/0566; G01N 2223/302; G01N 2223/345; G01N 2223/607

See application file for complete search history.

(56) References Cited

U.S. PATENT DOCUMENTS

| 4,489,425 A | 12/1984 | Borgonovi | |
| 4,561,062 A * | 12/1985 | Mitchell | G01N 23/207 378/72 |
| 5,148,458 A * | 9/1992 | Ruud | G01L 1/25 378/70 |
| 2004/0177700 A1 * | 9/2004 | Yokoyama | G01N 23/207 73/800 |

OTHER PUBLICATIONS

He, Baoping Bob et al., "Strain and Stress Measurements with a Two-Dimensional Detector", JCPDS-International Centre for Diffraction Data, 1999, pp. 501-508.
Tanaka, Keisuke et al., "Diffraction Measurements of Residual Macrostress and Microstress Using X-Rays, Synchrotron and Neutrons", JSME International Journal, Series A, Jul. 2004, vol. 47, No. 3, pp. 252-263.

\* cited by examiner

*Primary Examiner* — Anastasia Midkiff
(74) *Attorney, Agent, or Firm* — Birch, Stewart, Kolasch & Birch, LLP

(57) ABSTRACT

A stress analysis apparatus capable of improving the accuracy of a stress value, a method, and a program are provided. A stress analysis apparatus 100 that calculates a residual stress of a sample S includes an analysis unit configured to calculate an error as one of solutions by using an equation including an error term and prescribing a relationship between stress and strain with using measured values of diffracted X-rays with respect to a plurality of scattering vectors and a provisional value when the stress in a direction perpendicular to the surface of the sample S is constant, and a provisional value correction unit configured to correct the provisional value using the calculated error, and the analysis unit and the provisional value correction unit repeat the calculation of the error and the correction of the provisional value.

5 Claims, 10 Drawing Sheets

|  | DSR METHOD ||||||  COS α METHOD ||
|  | σ11 || σ12 || σ22 || σ11 | σ12 |
|  | STRESS VALUE | ESD | STRESS VALUE | ESD | STRESS VALUE | ESD | STRESS VALUE | STRESS VALUE |
| CALCULATION FROM RAW DATA | −1757.8 | 117.5 | −47.9 | 49.8 | −1.3 | 117.5 | − | − |
| RECALCULATION FROM THEORETICAL VALUE OF PEAK POSITION | −1757.8 | 0.0 | −47.9 | 0.0 | −1.3 | 0.0 | −1715.3 | −50.1 |

FIG. 7B

X-RAY STRESS ANALYSIS APPARATUS, METHOD, AND PROGRAM

BACKGROUND OF THE INVENTION

Field of the Invention

The present invention relates to a stress analysis apparatus that calculates a residual stress of a sample by using X-ray diffraction measurement results, a method, and a program.

Description of the Related Art

A cos α method, as a stress analysis method by single incidence of X-rays, is known. The cos α method is used in the case where a biaxial stress is analyzed from a single X-ray diffraction image obtained by a two-dimensional detector using the principle to be explained below.

If each symbol is defined as follows, a vertical strain $\varepsilon(\alpha)$ of a sample, which is observed at a position of $\alpha$ of a Debye-Scherrer ring, is expressed as expression (1) using vertical strains $\varepsilon_{11}$ and $\varepsilon_{22}$ and a shearing strain $\varepsilon_{12}$ on the device coordinate axes. That is, when a stress field is biaxial, the relationship of expression (1) holds for parameters on the two-dimensional detector.

$\psi_0$: an angle formed by the normal of the sample surface and the incident X-ray α: a circular angle of the Debye-Scherrer ring on the two-dimensional detector arranged vertical to the incident X-ray $2\eta_\alpha$: an angle formed by the incident X-ray and the diffracted X-ray, there is a relationship of $2\eta_\alpha = \pi - 2\theta_\alpha$ with respect to a diffraction angle $2\theta_\alpha$, $2\theta_\alpha$: a diffraction angle at the position α of the Debye-Scherrer ring $$\varepsilon(\alpha)=(\sin\psi_0 \sin\theta_\alpha-\cos\psi_0 \cos\alpha \cos\theta_\alpha)^2\varepsilon_{11}+\sin^2\alpha\cos^2\theta_\alpha\varepsilon_{22}+\sin\alpha\cos\theta_\alpha(\sin\psi_0 \sin\theta_\alpha-\cos\psi_0 \cos\alpha \cos\theta_\alpha)\varepsilon_{12} \quad (1)$$

Here, two values $\varepsilon_{\alpha 1}$ and $\varepsilon_{\alpha 2}$ are defined as follows.

$$\varepsilon_{\alpha 1} = \frac{\{\varepsilon(\alpha)-\varepsilon(\pi+\alpha)\}+\{\varepsilon(-\alpha)-\varepsilon(\pi-\alpha)\}}{2} \quad (2)$$

$$\varepsilon_{\alpha 2} = \frac{\{\varepsilon(\alpha)-\varepsilon(\pi+\alpha)\}-\{\varepsilon(-\alpha)-\varepsilon(\pi-\alpha)\}}{2} \quad (3)$$

If it is assumed that $2\theta_\alpha$ or $\eta_\alpha$ is constant with respect to α, the next relationship is obtained.

$\varepsilon_{\alpha 1}=S_2 \sin\psi_0 \cos\psi_0 \cos\alpha \sin 2\eta\sigma_{11}$ $\varepsilon_{\alpha 2}=S_2 \sin\psi_0 \sin\alpha \sin 2\eta\sigma_{12}$ (4)

If the plots of $\varepsilon_{\alpha 1}$ and $\varepsilon_{\alpha 2}$ to cos α and sin α are approximated by a straight line based on expression (4), $\sigma_{11}$ and $\sigma_{12}$ are obtained respectively from the slope. This method is the cos α method.

The cos α method is disclosed in, for example, Non-Patent Literature 1, as a method of finding a local stress from the measurement results by synchrotron X-rays of fiber-reinforced Ti alloy. According to Non-Patent Literature 1, it has been confirmed that the stress at the crack opening, which is obtained from the compression stress distribution calculated by the cos α method, agrees with the measured opening stress.

Further, In Non-Patent Literature 2, the application of the idea of a dilatation term to the expression of stress and strain is also described. In Non-Patent Literature 2, addition of $\varepsilon_{ph}$ of a pseudo hydrostatic strain component to the expression as a dilatation term is described. Then, Non-Patent Literature 2 claims that a stress value may be calculated due to this dilatation term even if the exact lattice constant when stress is zero is not known.

Non-Patent Literature

Non-Patent Literature 1: K. TANAKA, Y. AKINIWA, "Diffraction Measurements of Residual Macrostress and Microstress Using X-Rays, Synchrotron and Neutrons", JSME International Journal. Series A, v. 47, n. 3, July, 2004, p. 252-263

Non-Patent Literature 2: Baoping Bob He, Kingsley L. Smith, Strain and Stress Measurements with a Two-Dimensional Detector, JCPDS-International Centre for Diffraction Data 1999, P505

As described above, in the cos α method, by taking the constant term of the approximate straight line to be an independent variable, a large error resulting from the error of $d_0$ is removed. However, because the analysis is performed on the assumption that $2\theta_\alpha$ or $\eta_\alpha$, which is originally the function of α, is constant with respect to α, the scattering vector strictly in accordance with the Debye-Scherrer ring is not taken into consideration, and therefore, the calculation results include an error resulting from this assumption.

Further, in the case where the crystal particle size of a sample is coarse, it cannot be avoided to use the Debye-Scherrer ring generated with part of the ring missing as an analysis target, and therefore, it is no longer possible to apply the cos α method. On the other hand, an analysis method using a general expression without approximation such as the cos α method, is conceivable, but it is not possible to solve the expression unless some measures are taken, and if the value of the spacing of crystal lattice planes including an error is used, an error is also included in the calculation results.

SUMMARY OF THE INVENTION

The present invention has been made in view of such a circumstance, and its object is to provide a stress analysis apparatus capable of improving the accuracy of a stress value by taking a scattering vector into consideration, introducing an error term, and improving an iterative solution, a method, and a program.

(1) In order to achieve the above-described object, the stress analysis apparatus of the present invention is a stress analysis apparatus that calculates a residual stress of a sample includes an analysis unit configured to calculate, when a stress in a direction perpendicular to a surface of the sample is constant, an error as a solution of an equation including an error term and prescribing a relationship between stress and strain with measured values of diffracted X-rays with respect to a plurality of scattering vectors and a provisional value and a provisional value correction unit configured to correct the provisional value using the calculated error, and the analysis unit and the provisional value correction unit repeat the calculation of the error and the correction of the provisional value.

It is possible to improve the accuracy of a stress value by taking a scattering vector into consideration, introducing an error term, and improving an iterative solution in this manner. Further, even if the crystal particle size is coarse and a loss of data occurs, it is possible to obtain analysis results. Note that the above-described error term is, for example, a term representing an error of strain and the provisional value is a provisional value of the spacing of crystal lattice planes $d_0$ when there is no strain in the sample, but the error and the provisional value do not depend on such representation.

(2) Further, in the stress analysis apparatus of the present invention, the provisional value correction unit corrects the provisional value by approximating an error rate of the spacing of crystal lattice planes to be equal to an error of strain, the signs of the error being inverted. Due to this, it is possible to easily correct the provisional value of the spacing of crystal lattice planes in the strain-free state.

(3) Furthermore, the stress analysis apparatus of the present invention further includes an output unit configured to output each stress value as analysis results, the stress value obtained by substituting the final value of the corrected provisional value in the equation. It is possible to obtain each stress value by removing the error in this manner.

(4) Moreover, in the stress analysis apparatus of the present invention, the analysis unit calculates the solution of the equation by the least squares method. Due to this, it is possible to easily calculate an error and stress from an observation equation.

(5) In addition, the method of the present invention is a stress analysis method of calculating a residual stress of a sample including the steps of calculating, when a stress in a direction perpendicular to a surface of the sample is constant, an error as a solution of an equation including an error term and prescribing a relationship between stress and strain with measured values of diffracted X-rays with respect, to a plurality of scattering vectors and a provisional value and correcting the provisional value using the calculated error and the calculation of the error and the correction of the provisional value are repeated. It is possible to improve the accuracy of a stress value by taking a scattering vector into consideration, introducing an error term, and improving an iterative solution in this manner.

(6) Additionally, the program of the present invention is a stress analysis program for calculating a residual stress of a sample, the stress analysis program causing a computer to perform processing to calculate, when a stress in a direction perpendicular to a surface of the sample is constant, an error as a solution of an equation including an error term and prescribing a relationship between stress and strain with measured values of diffracted X-rays with respect to a plurality of scattering vectors and a provisional value, and processing to correct the provisional value using the calculated error and in that the calculation of the error and the correction of the provisional value are repeated. It is possible to improve the accuracy of a stress value by taking a scattering vector into consideration, introducing an error term, and improving an iterative solution in this manner.

According to the present invention, it is possible to improve the accuracy of a stress value by taking a scattering vector into consideration, introducing an error term, and improving an iterative solution.

BRIEF DESCRIPTION OF THE DRAWINGS

FIG. 7A is a graph in which the peak positions of the Debye-Scherrer ring are plotted and FIG. 7B is a table showing a comparison between stress values of raw data and stress values of theoretical values.

DETAILED DESCRIPTION OF THE INVENTION

Next, an embodiment of the present invention is explained with reference to the drawings. In order to make easy to understand explanation, the same symbols are used to indicate the same components in each drawing and duplicated explanation is omitted.

Configuration of Stress Analysis System

Figure 1:
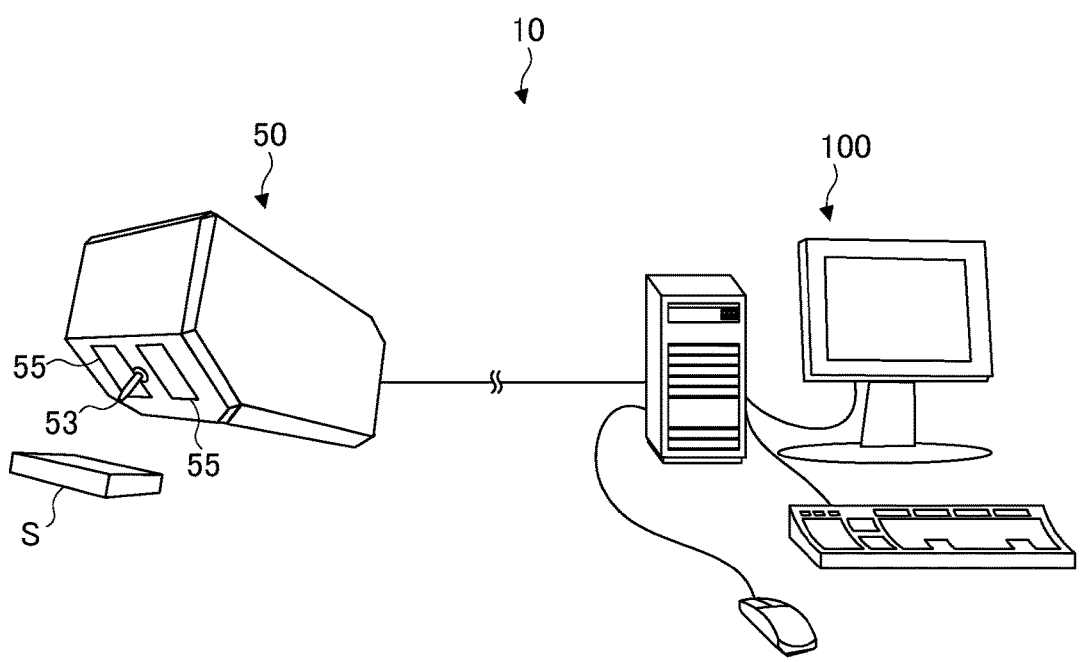
FIG. 1 is a schematic diagram showing a stress analysis system of the present invention.

FIG. 1 is a schematic diagram showing a stress analysis system 10. The stress analysis system 10 includes an X-ray diffraction apparatus 50 and a stress analysis apparatus 100, and it is possible for the X-ray diffraction apparatus 50 and the stress analysis apparatus 100 to perform transmission and reception of data therebetween. Note that, it is preferable for the X-ray diffraction apparatus 50 and the stress analysis apparatus 100 to be connected so as to be capable of communication, but it may also be possible to move data by using a storage medium.

Configuration of X-Ray Diffraction Apparatus

The X-ray diffraction apparatus 50 includes an X-ray generation unit, a pinhole collimator 53, and a detection unit 55. The X-ray generation unit generates X-rays and irradiates the generated X-rays toward the pinhole collimator 53. The pinhole collimator 53 collimates the irradiated X-rays and irradiates the surface of a sample having an isotropic structure when there is no strain with the collimated X-rays. The X-rays irradiated through the pinhole collimator 53 are diffracted by a specific crystal lattice plane of a sample S. At this time, the diffracted X-rays are irradiated in a cone-shaped area with the X-ray irradiation point as a vertex. The detection unit 55 is, for example, a two-dimensional semiconductor detector, provided on both sides of the pinhole collimator 53, and detects diffracted X-rays.

Figure 2:
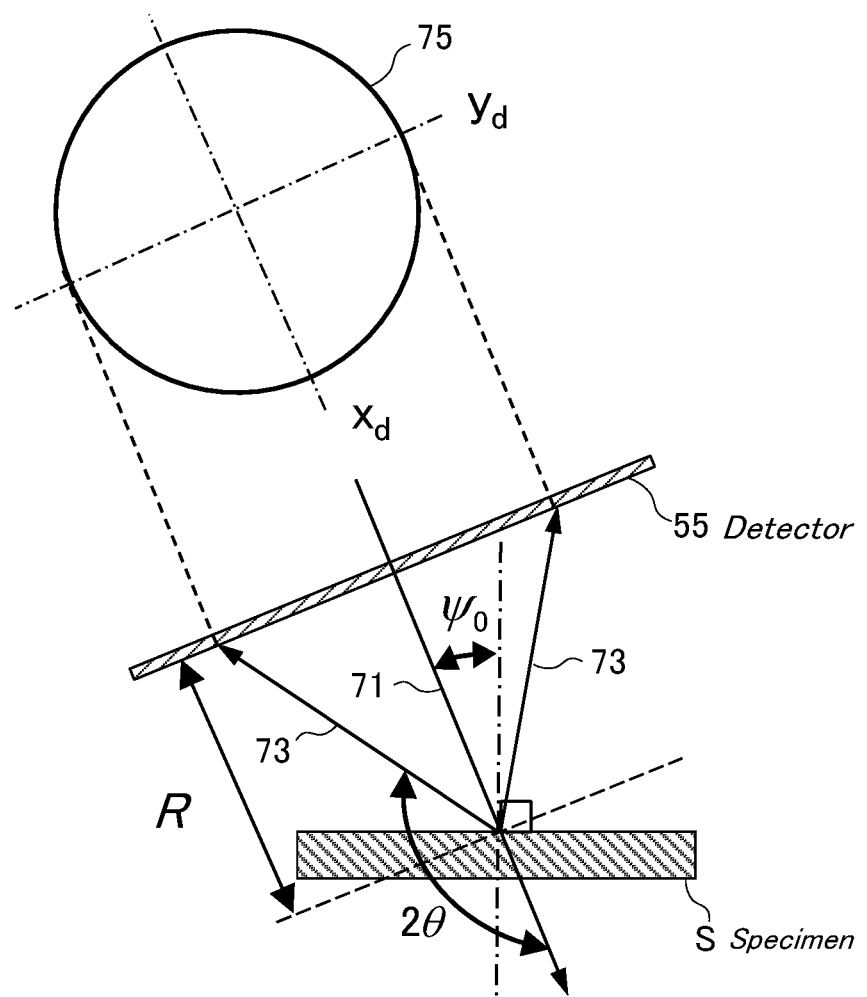
FIG. 2 is a schematic diagram showing an X-ray diffraction apparatus and a Debye-Scherrer ring.

FIG. 2 is a schematic diagram showing the X-ray diffraction apparatus 50 and a Debye-Scherrer ring 75. As shown in FIG. 2, a coordinate system, incident X-rays 71, diffracted X-rays 73, and the Debye-Scherrer ring 75 in the case where the surface of the sample S is irradiated with X-rays are shown. A specific portion of the sample S is irradiated with X-ray beams and the image of the Debye-Scherrer ring 75 is formed on the detection unit 55 by the diffracted X-rays. Further, $\psi_0$ is an angle formed by the normal of the surface of the sample S and the incident X-ray 71. In FIG. 2, $x_d$ and $y_d$ indicate the coordinate axes, respectively, on the surface of the detector 55.

Figure 3A:
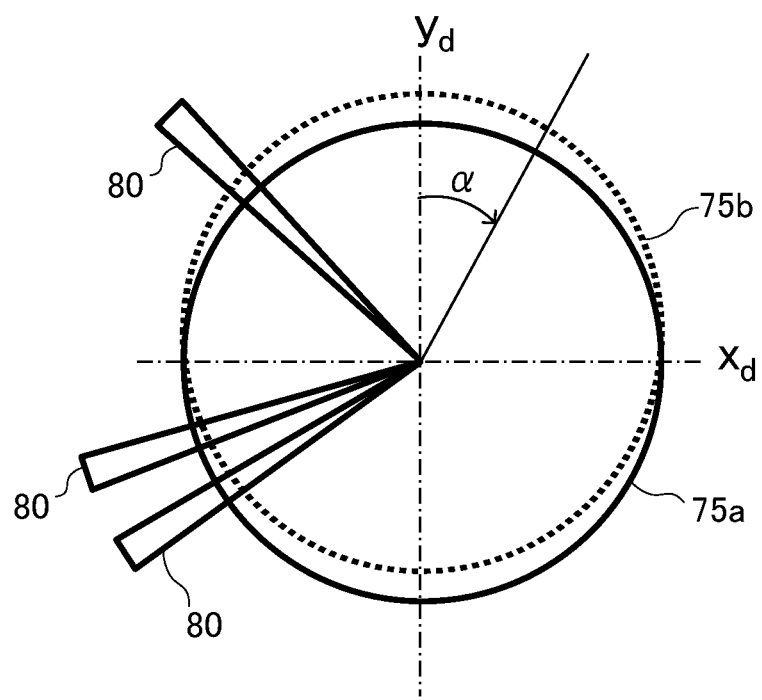
FIGS. 3A and 3B are a diagram showing a change in shape of the Debye-Scherrer ring with the sample distorted and a graph representing a change in peak position, respectively.
Figure 3B:
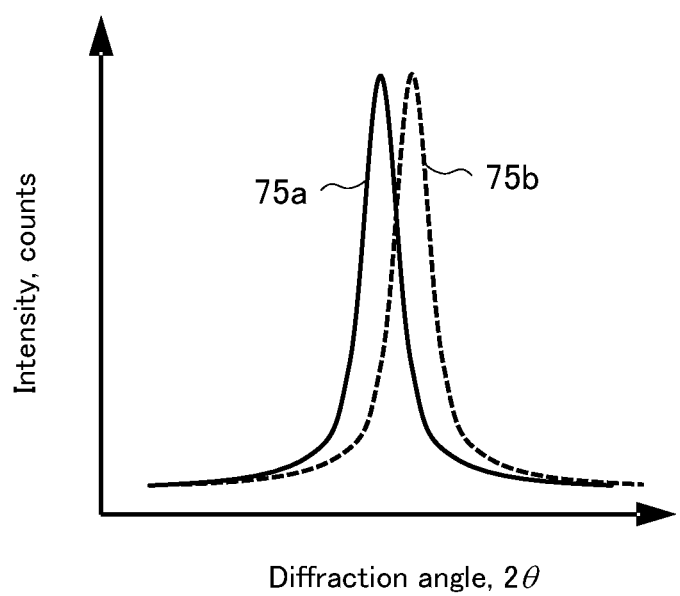

FIGS. 3A and 3B are a diagram showing a change in shape of the Debye-Scherrer ring 75 with the sample distorted and a graph representing a change in peak position of a diffraction angle 2θ profile, respectively. In the stress measurement using the Debye-Scherrer ring 75, in the case where there is strain in the specific portion of the sample that is irradiated with X-rays, a Debye-Scherrer ring 75b changed in shape in accordance with the strain of the sample occurs in a position deviated from a Debye-Scherrer ring 75a of a true circle when there is no strain. The diffraction angle 2θ profile of an integration range 80 for the same circular angle α is different between the Debye-Scherrer ring 75a and the Debye-Scherrer ring 75b. This Debye-Scherrer ring 75b can be detected by the detection unit 55. Then, for the detected Debye-Scherrer ring 75b, $d_{\varphi\psi}$ is obtained as a measured value and φ and ψ can be calculated as calculated values, and therefore, it is possible to calculate each stress value by solving the equation.

Figure 4:
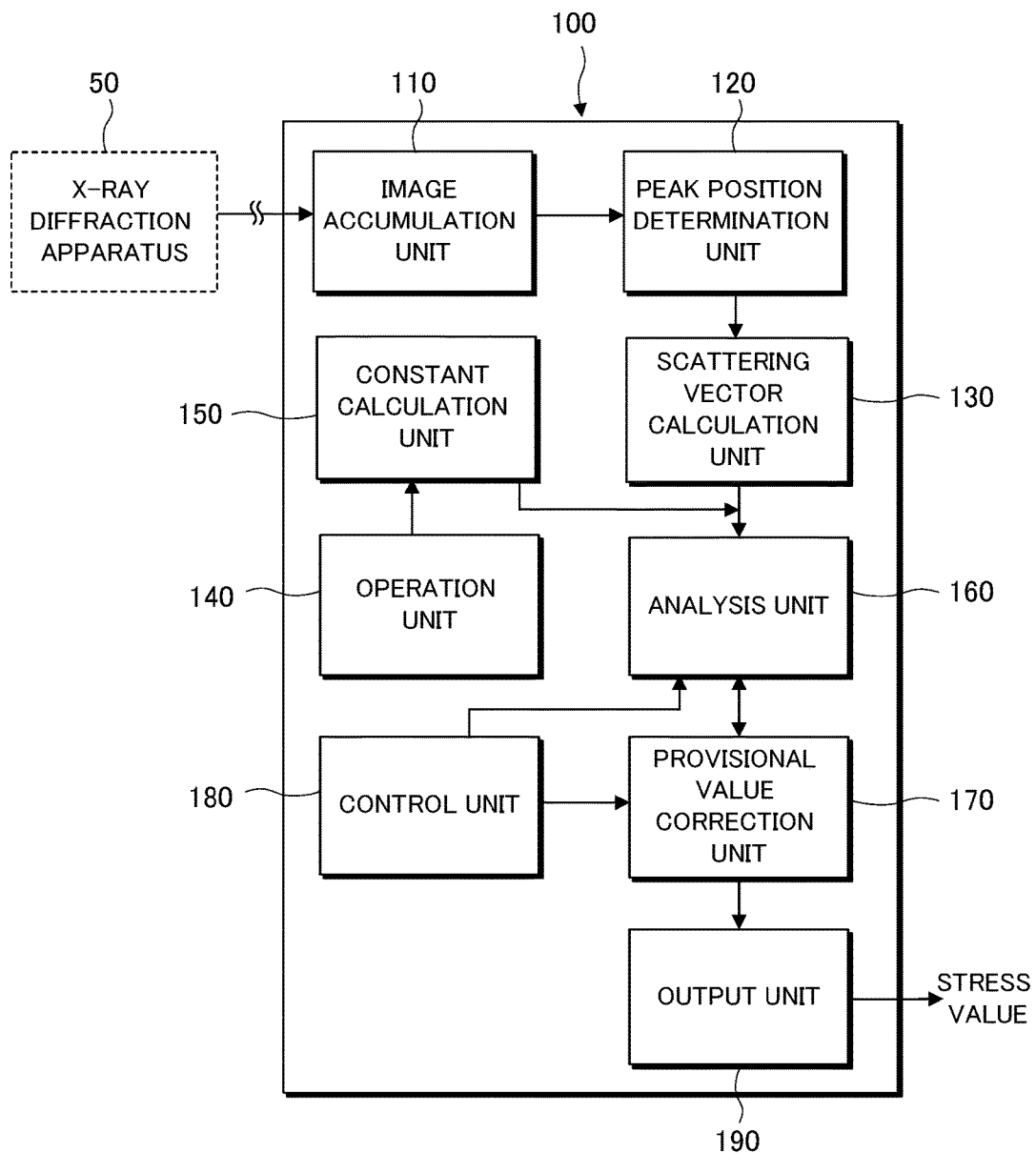
FIG. 4 is a block diagram showing a functional configuration of a stress analysis apparatus.

FIG. 4 is a block diagram showing a functional configuration of the stress analysis apparatus 100. As shown in FIG. 4, the stress analysis apparatus 100 includes an image accumulation unit 110, a peak position determination unit 120, a scattering vector calculation unit 130, an operation unit 140, a constant calculation unit 150, an analysis unit 160, a provisional value correction unit 170, a control unit 180, and an output unit 190 and calculates a residual stress of a sample from the data of the photographed Debye-Scherrer ring.

The image accumulation unit 110 accumulates data of an image of the Debye-Scherrer ring photographed by the X-ray diffraction apparatus 50 and input to the stress analysis apparatus 100. The peak position determination unit 120 determines 2θ corresponding to the peak position for each α of the Debye-Scherrer ring from the peak intensity distribution or the like. The scattering vector calculation unit 130 calculates the Euler angles φ and ψ as a scattering vector corresponding to each peak position 2θ for α.

The operation unit 140 includes, for example, a keyboard, a touch panel, etc., and receives an input of a user. It is possible for the user to input a condition to terminate loop processing, the initial value of a provisional value, the characteristic value of the sample, etc., to be described later, through the operation unit 140. The constant calculation unit 150 calculates constants $S_1$ and $S_2$ in expression (5), to be described later, by using Young's modulus and Poisson's ratio determined by the material of the sample.

The analysis unit 160 calculates an error as one of solutions by using an equation including an error term and prescribing a relationship between stress and strain with measured values of diffracted X-rays with respect to a plurality of scattering vectors and a provisional value when the stress in a direction perpendicular to the surface of the sample S is constant. Specifically, it is possible to find $\sigma_{ij}$ (i, j=1, 2) by measuring $d_{\varphi\psi}$ using diffracted X-rays at different φ and ψ and by using expression (9), to be described later, as an observation equation using those values. It is preferable for the analysis unit 160 to calculate the solution of the observation equation by, for example, the least squares method. Due to this it is possible to easily calculate an error and stress from the observation equation.

The provisional value correction unit 170 corrects the provisional value using the calculated error. It is preferable for the provisional value correction unit 170 to correct the provisional value by approximating that the error rate of the spacing of crystal lattice planes to be equal to an error of the strain the signs of which are inverted. Due to this, it is possible to easily correct the provisional value of the spacing of crystal lattice planes.

The control unit 180 causes the analysis unit and the provisional value correction unit to repeat the calculation of the error and the correction of the provisional value until a predetermined condition is satisfied. It is possible to improve the accuracy of a stress value by taking a scattering vector into consideration, introducing an error term, and improving an iterative solution in this manner. Further, it is possible to obtain analysis results even if the crystal particle size is coarse and a loss of data occurs. The predetermined condition is, for example, that the error becomes smaller than a predetermined numerical value. The output unit 190 outputs each stress value obtained as a solution of the equation, which is finally obtained after the above-described iterative processing is completed, as analysis results. It is possible to obtain each stress value by removing the error in this manner.

Operation of Stress Analysis Apparatus

Figure 5:
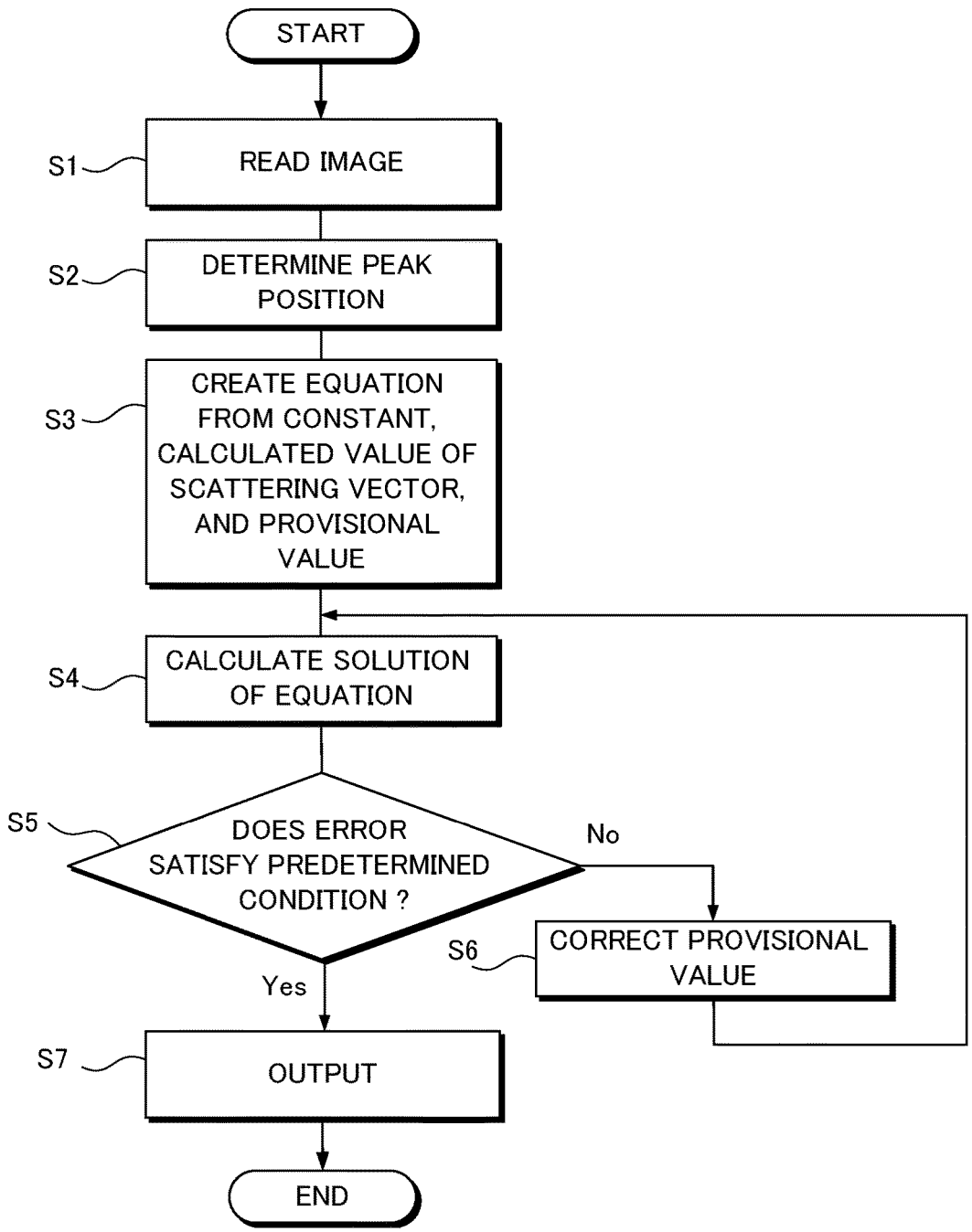
FIG. 5 is a flowchart showing an operation of the stress analysis apparatus.

An example of the operation of the stress analysis apparatus 100 configured as described above is explained. FIG. 5 is a flowchart showing the operation of the stress analysis apparatus 100. Note that, in the following explanation, in order to make explanation easy-to-see, symbols included in expression (10) or the like, to be described later, are used.

First, data of an image of a Debye-Scherrer ring photographed by the X-ray diffraction apparatus 50 and accumulated in the stress analysis apparatus 100 is read (step S1). Next, the peak position of the Debye-Scherrer ring is determined from the data of the image (step S2), the scattering vectors φ and ψ are calculated from the peak position, the constants $S_1$ and $S_2$ and a provisional value $d_{0(k)}$ are calculated, and an equation of the DRS (Direct Refinement Solution) method is created (step S3). A solution is calculated by analyzing the created equation (step S4).

Then, whether or not an error $\Delta\varepsilon_{(k)}$ satisfies the predetermined condition is determined (step S5) and in the case where the error $\Delta\varepsilon_{(k)}$ does not satisfy the condition, the provisional value $d_{0(k)}$ is corrected (step S6) and the processing returns to step S4. In the case where the error $\Delta\varepsilon_{(k)}$ satisfies the condition, a stress value $\sigma_{ij(k)}$ is output (step S7) and the processing is terminated.

Principle

Figure 6:
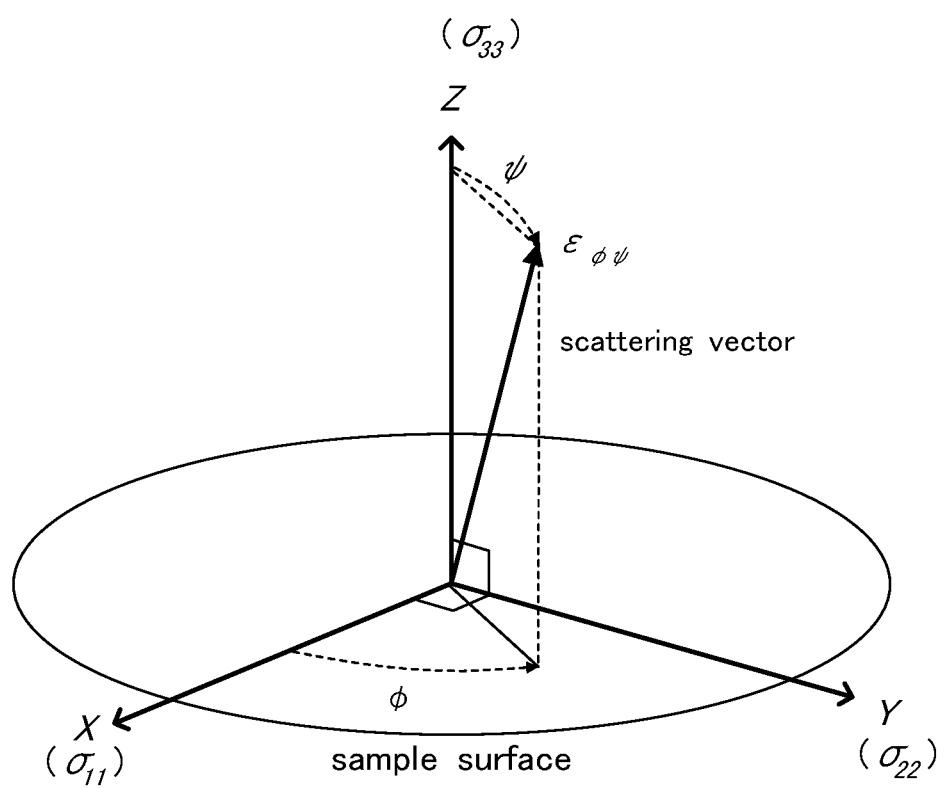
FIG. 6 is a schematic diagram showing a scattering vector by the Euler angles $\varphi$ and $\psi$ on the surface of a sample.

Next, the principle to calculate stress is explained. FIG. 6 is a schematic diagram showing a scattering vector by the Euler angles φ and ψ on the sample surface. In the device coordinate system, the relationship between a vertical strain $\varepsilon_{\varphi\psi}$ viewed from the orientation indicated by the Euler angles φ and ψ, and vertical stresses $\sigma_{11}$, $\sigma_{22}$, and $\sigma_{33}$ and shearing stresses $\sigma_{23}$, $\sigma_{13}$, and $\sigma_{12}$ on the device coordinate axes is defined as follows.

$$\varepsilon_{\varphi\psi} = \frac{1}{2}S_2\{(\sigma_{11}\cos^2\varphi + \sigma_{12}\sin 2\varphi + \sigma_{22}\sin^2\varphi)\sin^2\psi + \\ (\sigma_{13}\cos\varphi + \sigma_{23}\sin\varphi)\sin 2\psi + \sigma_{33}\cos^2\psi\} + S_1(\sigma_{11} + \sigma_{22} + \sigma_{33}) \tag{5}$$

Figure 8:
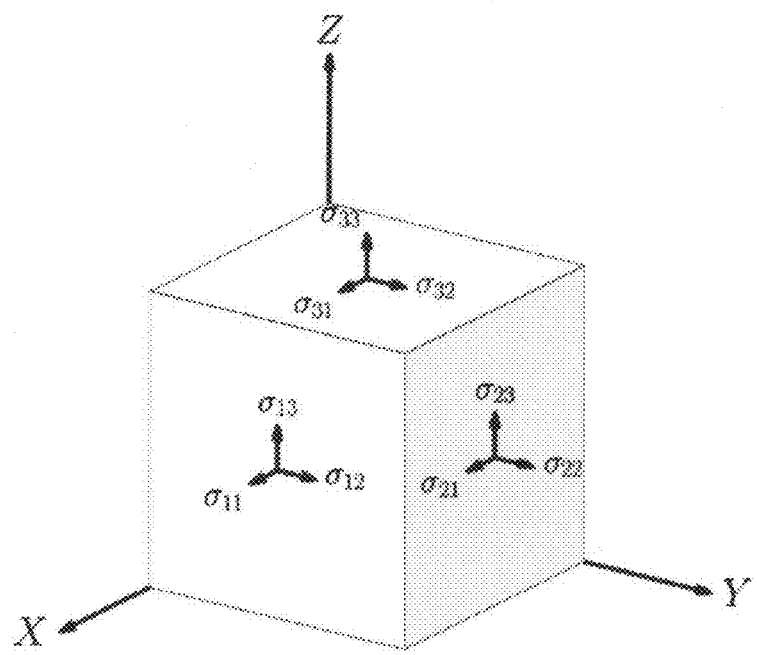
FIG. 8 is a diagram showing a shearing stresses on a device coordinate axes.

As shown in FIG. 8 (from "X-ray stress analysis technique using the optimization of d0 with error term Direct Refinement Solution (DRS) method", Rigaku Journal 32(2), 2016), σ23, σ13, σ12 are conventional symbols that are used like all, σ22, σ33. For example, σ23 shows a shear stress applied in Z axis direction on a plane perpendicular to Y axis.

Here, $S_1$ and $S_2$ are constants called X-ray elastic compliance and are expressed as follows by using Young's modulus E and Poisson's ratio.

$$S_1 = -\frac{\nu}{E} \tag{6}$$

-continued $$\frac{1}{2}S_2 = \frac{1+v}{E} \quad (7)$$

On the other hand, if X-ray diffraction is used, it is possible to measure the spacing of crystal lattice planes. If the spacing of crystal lattice planes spacing of spacing of crystal lattice planes measured in an optical system in which the orientation of the scattering vector of X-ray, i.e., the orientation of the normal of the crystal lattice plane to be measured is arranged so as to be φ and ψ is taken to be $d_{\varphi\psi}$, and the spacing of crystal lattice planes in the strain-free state is taken to be $d_0$, the strain $\varepsilon_{\varphi\psi}$ in the direction of φ and ψ is expressed as follows by using $d_{\varphi\psi}$ and $d_0$.

$$\varepsilon_{\varphi\psi} = \frac{d_{\varphi\psi} - d_0}{d_0} \quad (8)$$

Because $d_0$ is a value unique to the material, it is possible to theoretically find the stresses $\sigma_{11}$, $\sigma_{22}$, and $\sigma_{33}$ and $\sigma_{23}$, $\sigma_{13}$, and $\sigma_{12}$ from (5) and (6) described above by measuring the spacing of crystal lattice planes at six or more different combinations of φ and ψ.

However, in fact, $d_0$ changes easily depending on the state of the crystal, and therefore, it is not possible to know the exact $d_0$ in advance for all the samples and if the calculation of stress is performed by using the given $d_0$ and expression (5) as they are, there is a case where the calculation results include a large error. Further, it is not possible to solve a nonlinear simultaneous equation that also treats $d_0$ as a variable, which is created from the values of the spacing of crystal lattice planes measured at seven or more combinations of φ and ψ. Because of this, in the conventional stress analysis method, a calculation method that avoids such an error has been used.

If the analysis method such as this is used, it is possible to avoid a large error resulting from the error of $d_0$, but there still remains an error resulting from a model representing the relationship between strain and stress, which is employed in each analysis method. With the "DRS method" of the stress analysis method to be explained as the present embodiment, it is possible to obtain calculation results with a higher accuracy compared to the conventional analysis method by applying [1] and [2] mentioned below.

[1] Directly use a model most faithfully representing the relationship between strain and stress of an isotropic elastic material expressed by expression (5).

[2] Perfectly remove an error of the stress calculated value resulting from the error of $d_0$ by solving a nonlinear equation including both stress and $d_0$ as variables.

With the DRS method, in order to improve the calculation accuracy, calculation of stress is performed by using expression (5) most faithfully representing the relationship between stress and strain in an isotropic elastic material. However, in order to remove the error of the stress calculated value resulting from the error of $d_0$, the stresses other than $\sigma_{33}$ are calculated by using $d_0$ as a variable. At this time, the general solving method of a nonlinear equation, such as the Newton method that requires an initial value of the solution, is not used but a more efficient method that utilizes the structural feature of a problem as below is used. Note that, the reason why it is possible to solve the equation by using $d_0$ as a variable it $\sigma_{33}$ is fixed as described above will be described later.

From expressions (5) and (8), an equation such as below, which focuses on the spacing of crystal lattice planes, is created. Here, $d_{0(k)}$ is taken to be a constant, and therefore, this equation is linear. Further, $\sigma_{33}$ is taken to be a constant. For example, $\sigma_{33}=0$ is set. Here, $\Delta\varepsilon_{(k)}$ is a term representing an error of the observed value of strain generated by the error of the provisional value $d_{0(k)}$.

$$d_{\varphi\psi} = d_{0(k)}\{\varepsilon_{\varphi\psi}(\sigma_{ij(k)}) + \Delta\varepsilon_{(k)} + 1\} \quad (9)$$

Specifically, it is possible to express as expression (10).

$$d_{\phi\psi} = d_{0(k)}\left\{\frac{1}{2}S_2(\sigma_{11(k)} + \sigma_{12(k)}\sin 2\phi + \xi_{22(k)}\sin^2\phi)\sin^2\psi_{(k)} + S_1(2\sigma_{11(k)} + \xi_{22(k)}) + \Delta\varepsilon_{(k)} + 1\right\} \quad (10)$$

$$d_{\phi\psi} = d_0(\varepsilon_{\phi\psi} + 1)$$

$$\cos^2\phi = 1 - \sin^2\phi$$

$$\xi_{22} \equiv \sigma_{22} - \sigma_{11}$$

From the stress $\sigma_{ij(k)}$ obtained by solving this equation, a large error resulting from the error of $d_0$ is removed and if the stress is very close to the true value, $\Delta\varepsilon_{(k)}=0$ will hold. In other cases, $d_{0(k)}$ still includes an error that cannot be ignored and $\sigma_{ij(k)}$ calculated by using $d_{0(k)}$ also includes an error similarly. From expression (13) and expression (14) to be described later, $\Delta\varepsilon_{(k)} \approx -\Delta_{(k)}$ will hold. Therefore, by finding $d_{0(k+1)}$ as follows and calculating $\sigma_{ij(k+1)}$ and $\Delta\varepsilon_{(k+1)}$ by using $d_{0(k+1)}$, $\sigma_{ij(k+1)}$ becomes closer to the true value and $\Delta\varepsilon_{(k+1)}$ becomes closer to 0. By repeating this operation until $\Delta\varepsilon_{(k+1)}$ becomes sufficiently close to 0, $\sigma_{ij(k+1)}$ converges to the true value.

Error Term

If the stress is calculated by using the spacing of crystal lattice planes $d_{0(k)}$ in the strain-free state including an error, the value that is obtained also includes an error. Consequently, $d_{0(k)}$ is defined as expression (11), the value of $d_{0(k)}$ is improved by utilizing this relationship, and then, the calculation accuracy of stress is increased.

$$d_{0(k)} = d_0(1 + \Delta_{(k)}) \quad (11)$$

Further, strain $\varepsilon_{\varphi\psi(k)}$ including the error calculated from $d_{0(k)}$ and $d_{\varphi\psi}$ by using expression (5) is defined as expression (12).

$$\varepsilon_{\varphi\psi(k)} = \varepsilon_{\varphi\psi} + \Delta\varepsilon \quad (12)$$

It is possible to calculate $d_{0(k+1)}$ by performing calculation as follows based on expressions (11) and (12).

$$\varepsilon_{\varphi\psi(k)} = \frac{d_{\varphi\psi} - d_{0(k)}}{d_{0(k)}} \quad (13)$$

$$\varepsilon_{\varphi\psi} + \Delta\varepsilon_{(k)} = \frac{d_{\varphi\psi}}{d_0(1 + \Delta_{(k)})} - 1 \cong \frac{d_{\varphi\psi}}{d_0}(1 - \Delta_{(k)}) - 1$$

$$\therefore \Delta\varepsilon_{(k)} \cong -\frac{d_{\varphi\psi}}{d_0}\Delta_{(k)} \cong -\Delta_{(k)} \quad (14)$$

$$d_{0k+1} = \frac{d_{0k}}{1 - \Delta\varepsilon_k} \quad (15)$$

Because $\varepsilon_{\varphi\psi}$ is a value less than or equal to $10^{-3}$, and therefore, for example, if $\Delta$ is about $10^{-2}$, $\Delta\varepsilon$ becomes a value of several times $\varepsilon_{\varphi\psi}$. Consequently, the error of the stress calculated from the strain including such an error also includes an error of several times the true value. It is possible to avoid such an error by fixing the value of $\sigma_{33}$, solving the nonlinear equation of expression (10), finding the remaining stresses and the error term $\Delta\varepsilon$, and finding $d_{0(k+1)}$ by using expression (15). It is possible to improve the accuracy of the stress value by solving the equation using $d_{0(k+1)}$ closer to $d_0$ than $d_{0(k)}$.

Reason Why it is Possible to Solve Equation by Using $d_0$ as Variable if $\sigma_{33}$ is Fixed In a nonlinear equation (16) below derived from expression (5) by using $d_0$ also as a variable, the coefficient of $d_0$ becomes the sum of the linear combination of the coefficients of the other variables and the constant by a linear equation to find a modified value of the solution.

$$d_{\varphi\psi} = d_0 \left[ \frac{1}{2} S_2 \{ (\sigma_{11}\cos^2\varphi + \sigma_{12}\sin 2\varphi + \sigma_{22}\sin^2\varphi)\sin^2\psi + (\sigma_{13}\cos\varphi + \sigma_{23}\sin\varphi)\sin 2\psi + \sigma_{33}\cos^2\psi \} + S_1(\sigma_{11} + \sigma_{22} + \sigma_{33}) + 1 \right] \quad (16)$$

On the other hand, between the coefficients of the linear equation, the relationship of expression (17) always holds regardless of the values of $\varphi$ and $\psi$.

$$\frac{\partial d_{\varphi\psi}}{\partial \sigma_{11}} + \frac{\partial d_{\varphi\psi}}{\partial \sigma_{22}} + \frac{\partial d_{\varphi\psi}}{\partial \sigma_{33}} = \frac{1}{2} S_2 + 3 S_1 \quad (17)$$

Because of this, the column vector of the coefficient matrix of the linear equation to find the modified value of the solution becomes linearly dependent, and therefore, it is not possible to solve the equation that uses all the stresses and $d_0$ as variables. This is also true with the linear equation (12) that takes $d_0$ to be a constant and introduces the error term of $d_0$. However, if $\sigma_{33}$ is taken to be a constant, the relationship of expression (17) is no longer maintained. Consequently, it is possible to find the remaining stresses and $d_0$ or the error term of $d_0$.

EXAMPLE

Comparison of DRS Method and cos α Method

Figure 7A:
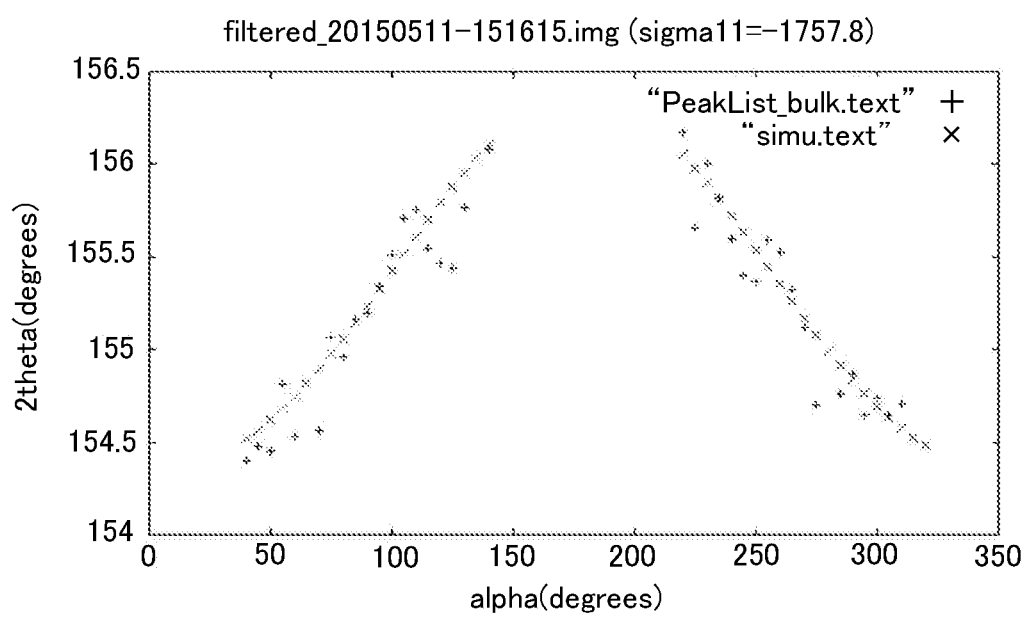

A stress analysis was performed by the cos α method and the method (DRS method) of the present embodiment using actual photographed data of a Debye-Scherrer ring. FIG. 7A is a graph obtained by plotting the peak positions of the photographed Debye-Scherrer ring and the theoretical peak positions on the coordinates of the circular angle α and the diffraction angle 2θ. FIG. 7B is a table in which the stress values calculated from the raw data and the stress values recalculated from the theoretical values of the peak positions are compared. Note that the calculation method of the theoretical value of the peak position will be described later.

In FIG. 7A, the peak position of the diffracted X-ray obtained in the process of the calculation using the actually measured data is represented by "+". The mark "x" in FIG. 7A represents the theoretical peak position in the case where the stresses are the above-described calculated values ($\sigma_{11}$=−1757.8, $\sigma_{12}$=−47.9, $\sigma_{22}$=−1.3).

In FIG. 7B, in the row of "Calculation from raw data", the stress values calculated by using the actually measured data are shown. On the other hand, the stress values calculated by using the theoretical peak positions are described in the row of "Recalculation from theoretical value of peak position" in the above-described table.

From this result, it is known that the original stress values ($\sigma_{11}$=−1715.3, $\sigma_{12}$=−50.1) can be calculated exactly from the theoretical peak positions by the "DRS method", but only the stress values with an accuracy of about two digits ($\sigma_{11}$−1715.3, $\sigma_{12}$=−50.1) can be calculated by the cos α method.

(Calculation Method of Theoretical Value)

The calculation of the theoretical value of the peak position was performed by the following procedures [1] to [6].

[1] From the spacing of crystal lattice planes $d_0$ in the strain-free state calculated by the DRS method, the arrangement of the optical system, and the circular angle α of a given Debye-Scherrer ring, the Euler angles $\varphi_{(k)}$ and $\psi_{(k)}$ of the scattering vector in the strain-free state at α are calculated.

[2] From $\varphi_{(k)}$ and $\psi_{(k)}$ obtained by the above-described calculation, $d_0$, and given stress values, the provisional value $d_{\varphi\psi(k)}$ of the spacing of crystal lattice planes, which would be observed at the Euler angles, is calculated by using expressions (5) and (8).

[3] From $d_{\varphi\psi(k)}$ obtained by the above-described calculation, improved values $\varphi_{(k+1)}$ and $\psi_{(k+1)}$ of the Euler angles are calculated as in the procedure [1].

[4] From $\varphi_{(k+1)}$ and $\psi_{(k+1)}$ obtained by the above-described calculation, an improved value $d_{\varphi\psi(k+1)}$ of the spacing of crystal lattice planes is calculated as in the procedure [2].

[5] The above-described procedures [3] and [4] are repeated until $|d_{\varphi\psi(k)} - d_{\varphi\psi(k+1)}|$ becomes, for example, less than or equal to $10^{-8}$.

[6] From the finally obtained spacing of crystal lattice planes $d_{\varphi\psi(k+1)}$, the diffraction angle $2\theta_{\varphi\psi}$ at given α is calculated.

DESCRIPTION OF REFERENCE SIGNS 10 stress analysis system
50 X-ray diffraction apparatus
53 pinhole collimator
55 detection unit
75a, 75b Debye-Scherrer ring
100 stress analysis apparatus
110 image accumulation unit
120 peak position determination unit
130 scattering vector calculation unit
140 operation unit
150 constant calculation unit
160 analysis unit
170 provisional value correction unit
180 control unit
190 output unit

What is claimed is:

1. A stress analysis apparatus that calculates a residual stress of a sample, comprising:
   an analysis unit configured to calculate, when a stress in a direction perpendicular to a surface of the sample is constant, an error as a solution of an equation including an error term and prescribing a relationship between stress and strain with measured values of diffracted X-rays with respect to a plurality of scattering vectors and a provisional value; and a provisional value correction unit configured to correct the provisional value using the calculated error, wherein the analysis unit and the provisional value correction unit repeat the calculation of the error and the correction of the provisional value, and wherein the provisional value correction unit corrects the provisional value by approximating an error rate of spacing of crystal lattice planes to be equal to an error of strain, the signs of the error being inverted.

2. The stress analysis apparatus according to claim 1 further comprising:

an output unit configured to output each stress value as analysis results, the stress value obtained by substituting the final value of the corrected provisional value in the equation.

3. The stress analysis apparatus according to claim 1, wherein the analysis unit calculates the solution of the equation by the least squares method.

4. A stress analysis method of calculating a residual stress of a sample, the method comprising the steps of:

calculating, when a stress in a direction perpendicular to a surface of the sample is constant, an error as a solution of an equation including an error term and prescribing a relationship between stress and strain with measured values of diffracted X-rays with respect to a plurality of scattering vectors and a provisional value; and correcting the provisional value using the calculated error, wherein the calculation of the error and the correction of the provisional value are repeated, and wherein the provisional value is corrected by approximating an error rate of spacing of crystal lattice planes to be equal to an error of strain, the signs of the error being inverted.

5. A computer readable non-transitory storage medium storing a stress analysis program for calculating a residual stress of a sample, the stress analysis program causing a computer to perform:

processing to calculate, when a stress in a direction perpendicular to a surface of the sample is constant, an error as a solution of an equation including an error term and prescribing a relationship between stress and strain with measured values of diffracted X-rays with respect to a plurality of scattering vectors and a provisional value; and processing to correct the provisional value using the calculated error, wherein the calculation of the error and the correction of the provisional value are repeated, and wherein the provisional value is corrected by approximating an error rate of spacing of crystal lattice planes to be equal to an error of strain, the signs of the error being inverted.

* * * * *